United States Patent [19]

Besecke et al.

[11] Patent Number: 5,393,917
[45] Date of Patent: * Feb. 28, 1995

[54] ISOLATION AND PURIFICATION OF OXADIMETHACRYLICS

[75] Inventors: Siegmund Besecke, Hameln; Andreas Deckers, Ludwigshafen; Harald Lauke, Mannheim, all of Germany

[73] Assignee: BASF Aktiengesellschaft, Ludwigshafen, Germany

[*] Notice: The portion of the term of this patent subsequent to Oct. 11, 2011 has been disclaimed.

[21] Appl. No.: 167,119

[22] Filed: Dec. 16, 1993

Related U.S. Application Data

[63] Continuation of Ser. No. 996,395, Dec. 23, 1992, abandoned.

[30] Foreign Application Priority Data

Dec. 24, 1991 [DE] Germany .............................. 4142912

[51] Int. Cl.$^6$ ............................................. C07C 69/73
[52] U.S. Cl. ...................... 560/181; 562/583; 564/193; 564/194; 564/201; 564/204; 564/207; 558/441; 558/449; 568/308; 568/309; 568/312; 568/317; 568/329
[58] Field of Search ..................... 560/181; 562/583; 564/193, 194, 201, 204, 207; 558/441, 449; 568/308, 309, 312, 317, 329

[56] References Cited

U.S. PATENT DOCUMENTS 4,889,948  12/1989  Mathias et al. ................. 560/181

OTHER PUBLICATIONS

Polymer Preprints, ACS, Div. of Polym. Chem. 31(1) (1990) 503 J. Dent. Res. 3 (1990), 69.
Mathias et al., "New Difunctional Methacrylate Ethers . . . ", Macromolecules, vol. 20, No. 8, 1987, pp. 2039–2041.

Primary Examiner—Paul J. Killos
Attorney, Agent, or Firm—Keil & Weinkauf

[57] ABSTRACT

A process for isolating and purifying oxadimethacrylics of the general formula I $$CH_2=C(A)CH_2-O-CH_2C(B)=CH_2 \qquad I$$

where A and B are selected from the group consisting of $-COOR^1$, $-COR^1$, $-CONR^2R^3$ and $-CN$ and $R^1$, $R^2$ and $R^3$ are each defined as follows:

$R^1$ is hydrogen, alkyl, substituted or unsubstituted cycloalkyl or cycloalkylalkyl, hydroxyalkyl, aminoalkyl, N-alkylaminoalkyl, N,N-dialkylaminoalkyl, substituted or unsubstituted aryl or arylalkyl, $R^2$ and $R^3$ are each hydrogen, alkyl, substituted or substituted cycloalkyl or cycloalkylalkyl, substituted or unsubstituted aryl or arylalkyl, comprises precipitating or crystallizing them from their solutions that contain at least one liquid hydrocarbon compound.

5 Claims, No Drawings

ISOLATION AND PURIFICATION OF OXADIMETHACRYLICS

This application is a continuation of application Ser. No. 07/996,395, filed on Dec. 23, 1992, abandoned.

The present invention relates to a process for isolating and purifying oxadimethacrylics of the formula I $$CH_2=C(A)CH_2-O-CH_2C(B)=CH_2 \qquad I$$

where A and B are selected from the group consisting of $-COOR^1$, $-COR^1$, $-CONR^2R^3$ and $-CN$ and $R^1$, $R^2$ and $R^3$ are each defined as follows:

$R^1$ is hydrogen, alkyl, substituted or unsubstituted cycloalkyl or cycloalkylalkyl, hydroxyalkyl, aminoalkyl, N-alkylaminoalkyl, N,N-dialkylaminoalkyl, substituted or unsubstituted aryl or arylalkyl, $R^2$ and $R^3$ are each hydrogen, alkyl, substituted or substituted cycloalkyl or cycloalkylalkyl, substituted or unsubstituted aryl or arylalkyl.

Oxadimethacrylics I are known for example from U.S. Pat. No. 4,889,948 and from Polymer Preprints, American Chemical Society, Division of Polymer Chemistry 31(1) (1990) 503.

Owing to their bifunctionality, these compounds are highly esteemed as monomeric building blocks, which are widely used for example as monomers for preparing homopolymers or as comonomers and crosslinkers. They can be obtained according to U.S. Pat. No. 4,889,948 starting from acrylics of type II, $H_2C=C(A)H$, but also starting from alcohols of type III, $H_2C=C(A)CH_2OH$. The reaction of alcohols of type III to form oxadimethacrylics I is carried out by heating, but reaction over one to two days, besides resulting in appreciable polymerization of the monomers, gives only moderate yields of oxadimethacrylics I.

Reacting acrylics of type II, $H_2C=C(A)H$, with formaldehyde in the presence of the tertiary amine 1,4-diazabicyclo[2.2.2] octane (DABCO®) produces according to U.S. Pat. No. 4,889,948 mainly alcohols of type III, $H_2C=C(A)CH_2OH$, only minor amounts of the oxadimethacrylics I, but higher (ether)homologs thereof of the formula Ia $$CH_2=C(A)CH_2-O-CH_2-[-O-CH_2]_n-C(A)=CH_2 \qquad Ia$$

where n=1-4 covers more than 90% of these homologs, and polymeric by-products. Besides this lack of specificity, further disadvantages of the reaction are the long reaction times (from 10 to 20 days) and appreciable polymerization at above room temperature.

When working up the crude product it is of course desirable to minimize the loss of product. And for the further processing of the oxadimethacrylics I, for example for preparing polymers, it will be readily understood that the compounds used should be as pure as possible.

J. Dent. Res. 3 (1990), 69, describes the isolation of the dimethyl ester of 2,2'-[oxybis(methylene)]dipropenoic acid ("oxadimethacrylic acid") by a complicated combination of extraction, distillation and subsequent column chromatography, but the yields achieved are only 15–25%.

Polymer Preprints, American Chemical Society, Division of Polymer Chemistry 31(1) (1990) 503 describes the purification of the crude mixture by column chromatography with subsequent recrystallization from methanol. Depending on the starting compound used, yields of from 37 to 82% are achieved.

U.S. Pat. No. 4,889,948 describes the direct fractional distillation of the crude mixture in a high vacuum. To obtain the desired purity the distillation is followed by a recrystallization in methanol. The products are only obtained in yields of <20%.

A further possibility described in U.S. Pat. No. 4,889,948 is first to extract the reaction mixture with water to remove the water-soluble constituents. The organic phase is then treated with sulfuric acid. Then the low boilers are distilled off, and the product is washed once more with water and finally recrystallized from methanol. The yields with this process are within the range from 10 to 20%.

It is an object of the present invention to overcome the disadvantages described and provide a simple and industrially utilizable process for isolating and purifying oxadimethacrylics.

We have found that this object is achieved by a process for isolating and purifying oxadimethacrylics of the formula I $$CH_2=C(A)CH_2-O-CH_2C(B)=CH_2 \qquad I$$

where A and B are selected from the group consisting of $-COOR^1$, $-COR^1$, $-CONR^2R^3$ and $-CN$ and $R^1$, $R^2$ and $R^3$ are each defined as follows:

$R^1$ is hydrogen, alkyl, substituted or unsubstituted cycloalkyl or cycloalkylalkyl, hydroxyalkyl, aminoalkyl, N-alkylaminoalkyl, N,N-dialkylaminoalkyl, substituted or unsubstituted aryl or arylalkyl, $R^2$ and $R^3$ are each hydrogen, alkyl, substituted or substituted cycloalkyl or cycloalkylalkyl, substituted or unsubstituted aryl or arylalkyl, which comprises precipitating or crystallizing them from their solutions that contain at least one liquid hydrocarbon compound.

From observations to date, the nature of the radicals $R^1$, $R^2$ and $R^3$ has basically no effect on the process of the invention.

The substituents preferably have the following meanings:

$R^1$ hydrogen;

$C_1$–$C_{18}$-alkyl, preferably $C_1$–$C_{12}$-alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl and stearyl, particularly preferably $C_1$–$C_4$-alkyl such as methyl, ethyl, n-propyl, isopropyl, n-butyl, isobutyl, sec-butyl, tert-butyl;

$C_3$–$C_8$-cycloalkyl such as cyclopropyl, cyclopentyl, cyclohexyl, cycloheptyl, cyclooctyl, 4-methylcyclohexyl, 4-methoxycyclohexyl, 2,4,6-trimethylcyclohexyl;

$C_3$–$C_8$-cycloalkyl-$C_1$–$C_5$-alkyl such as cyclopropylmethyl, cyclopentylmethyl, cyclohexylmethyl, cyclopropylethyl, cyclopentylethyl, cyclohexylethyl, cyclopropylpropyl, cyclopentylpropyl, cyclohexylpropyl, cyclopentylbutyl, cyclohexylbutyl, cyclopentylpentyl, cyclohexylpentyl, cyclooctylpentyl; hydroxy-$C_1$–$C_5$-alkyl such as hydroxymethyl, 2-hydroxyethyl, 2-hydroxypropyl, 3-hydroxypropyl, 4-hydroxybutyl, 5-hydroxypentyl, 2,2-dimethyl-3-hydroxypropyl;

amino-$C_1$-$C_5$-alkyl such as aminomethyl, 2-aminoethyl, 3-aminopropyl, 4-aminobutyl, 5-aminopentyl;

N-$C_1$-$C_4$-alkylamino-$C_1$-$C_5$-alkyl such as N-methylaminomethyl, 2-(N-methylamino)ethyl, 3-(N-methylamino)-propyl, 4-(N-methylamino)butyl, 5-(N-methylamino)-pentyl, N-ethylaminomethyl, N-n-propylaminomethyl, N-n-butylaminomethyl;

N,N-di($C_1$-$C_4$-alkyl)amino-$C_1$-$C_5$-alkyl such as N,N-dimethylaminomethyl, 2-(N,N-dimethylamino)ethyl, 3-(N,N-dimethylamino)propyl, 4-(N,N-dimethylamino)-butyl, 5-(N,N-dimethylamino)pentyl, N,N-diethylaminomethyl, N,N-di(n-propyl)aminomethyl, N,N-di-(isopropyl)aminomethyl, N,N-di(n-butyl)aminomethyl, N-ethyl-N-methyl-aminomethyl, N-methyl-N-propylaminomethyl;

$C_6$-$C_{18}$-aryl such as phenyl, naphthyl, anthracenyl, phenantrenyl, azulenyl, biphenylenyl, triphenylenyl, preferably phenyl, it being possible for the aryl radicals to carry up to three of the groups mentioned under $R^4$;

$C_6$-$C_{18}$-aryl-$C_1$-$C_4$-alkyl, preferably phenyl-$C_1$-$C_4$-alkyl such as benzyl, 2-phenylethyl, 3-phenylpropyl, 4-phenylbutyl, particularly preferably benzyl, 2-phenylethyl, 3-phenylpropyl, it being possible for the aryl groups to carry up to three of the groups mentioned under $R^4$;

$R^2$, $R^3$ $C_1$-$C_{18}$-alkyl such as mentioned for $R^1$, including particularly preferably $C_1$-$C_4$-alkyl such as methyl, ethyl, n-propyl, isopropyl, n-butyl, sec-butyl, isobutyl, tert-butyl;

$C_3$-$C_8$-cycloalkyl such as cyclopropyl, cyclopentyl, cyclohexyl, cycloheptyl, cyclooctyl, 4-methylcyclohexyl, 2,4,6-trimethylcyclohexyl;

$C_6$-$C_{18}$-aryl as mentioned for $R^1$ preferably phenyl, which may carry up to three of the groups mentioned under $R^4$;

$C_6$-$C_{18}$-aryl-$C_1$-$C_4$-alkyl such as mentioned for $R^1$, preferably phenyl-$C_1$-$C_4$alkyl, particularly preferably benzyl, 2-phenylethyl, 3-phenylpropyl, wherein the phenyl group may carry up to three of the groups mentioned under $R^4$; and $R^4$ halogen such as fluorine, chlorine, bromine and iodine, $C_1$-$C_{22}$-alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl and n-docosyl, preferably $C_1$-$C_{12}$ alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl and stearyl, particularly preferably $C_1$-$C_4$-alkyl such as methyl, ethyl, n-propyl, isopropyl, n-butyl, isobutyl, sec-butyl, tert-butyl;

$C_1$-$C_4$-alkoxy such as methoxy, ethoxy, n-propoxy and n-butoxy, carboxyl, $C_1$-$C_4$-alkoxy-carbonyl such as methoxycarbonyl, ethoxycarbonyl, n-propoxycarbonyl and n-butoxycarbonyl, aminocarbonyl, $C_1$-$C_4$-alkyl-aminocarbonyl such as methylaminocarbonyl, ethylaminocarbonyl, n-propylaminocarbonyl and n-butyl-aminocarbonyl, di($C_1$-$C_4$-alkyl)aminocarbonyl such as dimethylaminocarbonyl, diethylaminocarbonyl, di(n-propyl)aminocarbonyl and di(n-butyl)aminocarbonyl, nitrilo, nitro, amino, $C_1$-$C_4$-alkylamino such as methylamino, ethylamino, n-propylamino and n-butylamino, di($C_1$-$C_4$-alkyl)amino such as dimethylamino, diethylamino, di(n-propyl)amino and di(n-butyl)amino.

The process of the invention precipitates or crystallizes oxadimethacrylics I from solutions thereof that contain at least one hydrocarbon compound that is liquid at room temperature. This hydrocarbon compound may be present in these solutions from the start or added later.

In general, the process of the invention is employed for working up reaction mixtures which, as well as the oxadimethacrylic, may in general contain further substances such as starting materials, catalysts, stabilizers, etc. Of course, the process of the invention can also be used for purifying oxadimethacrylics.

The solubility-reducing hydrocarbon compound can be used right from the start for preparing the solution. In general it is advantageous not to add it to the solution of the oxadimethacrylic until the precipitation or crystallization is to be commenced.

The hydrocarbon compounds used will in general have a boiling point within the range from 20° to 200° C., preferably from 35° to 130° C., such as aliphatic, cycloaliphatic or aromatic hydrocarbons or mixtures thereof. Examples are n-pentane, n-hexane, n-heptane, n-octane, n-nonane, n-decane and their branched isomers, cyclopentane, cyclohexane, cycloheptane, cyclooctane and $C_1$-$C_4$-alkyl-substituted cycloaliphatics such as methylcyclopentane and methylcyclohexane, and aromatic hydrocarbons such as benzene, toluene and o-, m- and p-xylene.

The hydrocarbon compound is in general used in a weight ratio of hydrocarbon compound to oxadimethacrylic I of from 1:1 to 100:1, preferably from 1:1 to 10:1, particularly preferably from 2:1 to 4:1.

It is preferable for the temperature at the start of the crystallization to be some 5°–15° C. below the boiling point of the hydrocarbon compound in order that the concentration of oxadimethacrylic I in the hydrocarbon compound may be maximized. Of course, it is also possible to work at other temperatures, for example at room temperature. However, in general the range employed is from 20° to 200° C., preferably from 40° to 130° C., so that it may be necessary to employ pressures higher than atmospheric pressure. In general, the pressure range employed is from 70 to 250 kPa, preferably atmospheric pressure.

If the hydrocarbon compound is not added until the crystallization is to be commenced, or if the hydrocarbon compound is immiscible or only partly miscible with the particular solvent, it can be advantageous, prior to the crystallization, to subject the mixture to intensive mixing by a conventional method such as shaking, stirring or liquid-liquid extraction. This step can be carried out in one or more stages, batchwise or continuously. The temperature for this operation is advantageously within the abovementioned range from 20° to 200° C., preferably from 40° to 130° C.

For recrystallization the solutions employed generally contain the oxadimethacrylic in amounts within the range from 5 to 50, preferably from 10 to 30, % by weight. The solvents used here are in general the abovementioned hydrocarbon compounds.

The subsequent crystallization of the oxadimethacrylic I is in general carried out at from −80° to 30° C., preferably from −30° to 20° C. The crystalline product is then separated off in a conventional manner, for example by filtration or centrifuging, and dried in a conventional manner.

After the crystallization process it is possible, if two or more liquid phases are present, to separate off the phase that is not rich in the hydrocarbon compound and subject it to a renewed workup cycle in order that the remaining quantities of oxadimethacrylic I may be isolated as well. This operation can be repeated ad infinitum and be carried out batchwise or continuously.

The procedure in the case of other solutions or mixtures that contain oxadimethacrylics, for example in the case of reaction mixtures obtained in the synthesis of oxadimethacrylics, is basically the same as described above. In general, there is no need for expensive preliminary purification operations such as distillation, extraction or chromatography, but there are solutions or mixtures where such operations are useful. This is true in general of reaction mixtures in which the oxadimethacrylic I was not formed as main product. Furthermore, it can for example be advantageous to remove from reaction mixtures excess starting materials such as acrylics prior to the crystallization.

A particular embodiment concerns the isolation and purification of reaction mixtures obtained in the synthesis of oxadimethacrylics by one of the following processes A) reaction of an acrylic of the formula II $$H_2C=C(A)H \qquad \qquad II$$

with formaldehyde or a formaldehyde donor in the presence of oxygen, of at least one tertiary amine and preferably of at least one polymerization inhibitor to form the alcohol of the formula III $$H_2C=C(A)CH_2OH \qquad \qquad III$$

and subsequent conversion of alcohol III
b1) with isolation thereof or
b2) without isolation thereof into the oxadimethacrylic I, $CH_2=C(A)CH_2—O—CH_2C(A)=CH_2$, by heating in the presence of oxygen, of at least one tertiary amine and preferably of at least one polymerization inhibitor, or B) conversion of alcohol III into the oxadimethacrylic I, $CH_2=C(A)CH_2—O—CH_2C(A)=CH_2$, by heating in the presence of oxygen, of at least one tertiary amine and preferably of at least one polymerization inhibitor, or C) reaction of a mixture of two different acrylics of the formulae II and IIa $$H_2C=C(A)H \qquad \qquad II$$
$$H_2C=C(B)H \qquad \qquad IIa$$

with formaldehyde or a formaldehyde donor compound in the presence of oxygen, of at least one tertiary amine and preferably of at least one polymerization inhibitor to form the alcohols of the formulae III and IIIa $$H_2C=C(A)CH_2OH \qquad \qquad III$$
$$H_2C=C(B)CH_2OH \qquad \qquad IIIa$$

and then converting either a) the reaction mixture containing these alcohols, or
b) the isolated alcohols into the oxadimethacrylic I, $CH_2=C(A)CH_2—O—CH_2C(B)=CH_2$, by heating in the presence of oxygen, of at least one tertiary amine and preferably of at least one polymerization inhibitor, or D) reaction of an acrylic II with formaldehyde or a formaldehyde donor compound in the presence of oxygen, of at least one tertiary amine and of at least one polymerization inhibitor to form the alcohol III and subsequent reaction of the isolated alcohol III, or of the reaction mixture containing the non-isolated alcohol III, with a further, different alcohol IIIa by heating in the presence of oxygen, of at least one tertiary amine and preferably of at least one polymerization inhibitor to form the oxadimethacrylic I, $CH_2=C(A)CH_2—O—CH_2C(B)=CH_2$, or E) conversion of a mixture of two different alcohols III and IIIa into the oxadimethacrylic I, $CH_2=C(A)CH_2—O—CH_2C(B)=CH_2$ by heating in the presence of oxygen, of at least one tertiary amine and of at least one polymerization inhibitor.

The acrylics II required for these reactions are either commercially available or obtainable by methods known per se, for example by esterification, transesterification, amidation or aminolysis (see H. Rauch-Puntigam et al., Chemie, Physik und Technologie der Kunststoffe, vol. 9, Springer Verlag, Berlin, 1967), from the corresponding readily available acrylic precursors such as acrylic acid and known derivatives thereof.

The corresponding alcohols III are either known (see EP-B-184,731) or obtainable from the acrylics II by one of the above-indicated processes.

The formaldehyde can be used in gas form, and liquid form, for example as an aqueous solution such as formalin or in the form of a solution in an alcohol, or in solid form, for example as paraformaldehyde, trioxane or tetroxocane, or as a hemiacetal.

Suitable tertiary a mines are open-chain aliphatic or cyclic tertiary amines such as trimethylamine, triethylamine, tri-n-propylamine, triisopropylamine, tri-n-butylamine, triisobutylamine, tri-n-pentylamine, methyldiisopropylamine, N,N-diethylisopropylamine, N,N-dimethylethylamine, N,N-dimethylisopropylamine, tri-2-ethylhexylamine, N-methyldiethylamine, N,N-dimethyl-n-propylamine, N,N-dimethyl-n-butylamine, N,N-dimethyl-isobutylamine, N,N-dimethyl(2-ethylhexyl)amine, N,N-diisopropyl(2-ethylhexyl)amine, N,N-di-n-butyl(2-ethylhexyl)amine, N-methyl-di(2-ethylhexyl)amine, N-n-butyl(2ethylhexyl)amine, N-isobutyl-di(2-ethylhexyl)amine, quinuclidine and 1,4-diazabicyclo[2.2.2]octane (DABCO®), preferably quinuclidine and DABCO®, particularly preferably DABCO®.

The polymerization inhibitors used are in general the usual ones such as hydroquinone, hydroquinone monomethyl ether, p-benzoquinone, phenol, 2,6-dimethylphenol, 2,6-di-tert-butylphenol, methylene blue, diphenylamine, cupric oleate, ferric acetylacetonate, pyrocatechol, preferably hydroquinone monomethyl ether and hydroquinone monoethyl ether.

The oxygen can be passed in pure form or in the form of a mixture with nonreactive gases, preferably air, over or through the reaction mixture.

In the reaction of the acrylic II, or of the mixture of II and IIa, to form the oxadimethacrylic I via the alcohol compound III, the acrylic compound II, or the mixture II and IIa, and the formaldehyde are in general used in the first stage in a molar ratio of acrylic II, or mixture II and IIa, to formaldehyde of from 1:1 to 8:1, preferably from 1.0:1 to 2.5:1.

In this reaction the tertiary amine is preferably used in a molar ratio of formaldehyde to amine of from 1:1 to 200:1, preferably from 2:1 to 100:1, particularly preferably from 4:1 to 50:1.

The polymerization inhibitor is in general used in amounts of from 10 to 1000 mg per kg of acrylic II or mix II and IIa.

The amount of oxygen used ranges in general from 0.01 to 100, preferably from 0.1 to 20, l/h per kg of acrylic II or mix II and IIa. If air is used as oxygen donor, the gas rate will in general range from 0.01 to 1000, preferably from 1 to 250, l/h per kg of acrylic II or mix II and IIa.

The reaction is in general carried out at from 10° to 100° C., preferably at from 40° to 80° C., particularly preferably at from 60° to 75° C. Furthermore, the reaction is in general carried out under atmospheric pressure. However, it can also be carried out under reduced or superatmospheric pressure. The employment of superatmospheric pressure is advisable in particular when the reaction is carried out at above 80° C.

Furthermore, the reaction is in general carried out without solvent. However, the reaction can also be carried out in the presence of a suitable solvent such as a $C_5$–$C_8$-alkane, preferably n-pentane, n-hexane, n-heptane, n-octane, isooctane, a carboxylic ester such as ethyl acetate or an aromatic solvent such as benzene, toluene and xylenes, particularly preferably n-hexane, isooctane and toluene, or mixtures thereof.

The reaction time depends chiefly on the reaction temperature, but will in general range from 1 to 6 h.

The resulting alcohol III or mix III and IIIa can be isolated by a conventional workup method such as distillation or chromatography.

In the second stage, starting from alcohol III or from mix III and IIIa, the type and amount of amine, of polymerization inhibitor and of solvent are in general chosen as in the first stage. The oxygen rate will in general be within the range from 0.01 to 1000, preferably from 0.1 to 50, l/h per kg of alcohol compound III or mix III and IIIa. If air is used as oxygen donor, the gas rate will in general be within the range from 0.1 to 1000, preferably from 1 to 500, l/h per kg of alcohol compound III or mix III and IIIa.

The second stage conversion reaction (alcohol III to oxadimethacrylic I) is in general carried out at from 100° to 200° C., preferably at from 100° to 150° C., and at a pressure which in general will range from 70 to 300 kPa, but which preferably will be atmospheric pressure.

The water of reaction can in general be removed from the reaction mixture by distillation, preferably by rectification.

For this purpose it is a good idea to add an entrainer to the reaction mixture. Suitable entrainers for this purpose are for example aliphatic, cycloaliphatic and aromatic hydrocarbons such as n-hexane, n-heptane, isooctane, benzene, toluene, xylene, cyclohexane, and carboxylic esters such as ethyl acetate, or the acrylic II if it has not been separated off prior to the reaction. The entrainer will in general be selected to have a boiling point within the range from 80° to 200° C.

The reaction time is dependent on the usual parameters such as temperature, pressure and quantities of the starting materials and will in general range from 4 to 12 h.

If the reactions starting from the acrylic II or mix II and IIa are carried out in a single stage, i.e. without isolating the alcohol III or the mixture of III and IIIa, it is advantageous, prior to the conversion into the oxadimethacrylic I, to separate off the excess acrylic II or mixt II and IIa still present, for example by distillation. However, this can also be done after the conversion into the oxadimethacrylic I.

If one of the processes A), C) and D) is employed it is particularly preferable for the generally excess acrylic II and/or IIa to be distilled off before commencement with the isolation and purification by crystallization. It is similarly advantageous to remove the water of reaction formed in processes A) to E) prior to the crystallization, for example by distillation.

From observations to date the workup by crystallization gives the oxadimethacrylics I in a purity $\geq 90\%$.

The oxadimethacrylics obtained by the process of the invention can be polymerized in a conventional manner (see U.S. Pat. No. 4,889,948). Furthermore, they can also be converted by 1,6-intra-intermolecular cyclopolymerization into cyclic ethers, which are used for example in dental medicine (see Polymer Preprints, 31(1), 1990, 503).

EXAMPLES

EXAMPLE 1

Preparation of dimethyl 2,2'-[oxybis(methylene)]dipropenoate starting from methyl acrylate and formaldehyde a) With Workup by Chromatography

A mixture of 860 g (10 mol) of methyl acrylate, 150 g (5 mol) of paraformaldehyde, 56 g (0.5 mol) of DABCO ®((1,4-diazabicyclo[2.2.2]octane) and 172 g of hydroquinone monomethyl ether was heated at 75° C. for 1.75 h, while air was passed through the mixture at the same time at a rate of 10 l/h. Then with continued heating excess methyl acrylate was distilled off to such an extent that the temperature of the reaction mixture at the base of the column rose to 135° C. Thereafter the water of reaction was distilled off at 135° C. in the course of 4 h using the methyl acrylate still present as an azeotropic entrainer. Thereafter preparative column chromatography of the distillation residue over silica gel using 20/80 ethyl acetate/hexane as mobile phase yielded 64 g (12%) of methyl 2-hydroxymethylacrylate,
460 g (86%) of dimethyl 2,2'-[oxybis(methylene)]dipropenoate and
2.5 g (2%) of higher homologs of the oxadimethacrylic.

b) With Workup by Crystallization

The experiment of 1a) was repeated with the same quantities under the same conditions. However, after the water of reaction had been distilled off, the residue was cooled down to 60° C., admixed with 1400 g of n-hexane and stirred at 60° C. for one hour. Thereafter the bottom layer was separated off and the top layer was cooled down with stirring to 0° C. This precipitated some of the dimethyl ester in the form of fine white crystals. Filtration, washing with 300 ml of 0° C. n-hexane and drying at 25° C./100 mbar yielded 482 g (90%) of the dimethyl ester in a purity of 95%. Concentrating the mother liquor under reduced pressure, renewed addition of n-hexane at 60° C. and repeated crystallization yielded a further 21 g of the dimethyl ester in a purity of 92%.

EXAMPLE 2

Preparation of dicyclo 2,2'-[oxybis(methylene)]bis-2-propenoate a) Workup by Chromatography

A mixture of 308 g (2 mol) of cyclohexyl acrylate, 30 g (1 mol) of paraformaldehyde, 11.2 g (0.1 mol) of DABCO ® and 172 mg of hydroquinone monomethyl ether was heated at 75° C. for 6 h while air was passed through the mixture at the same time at a rate of 10 l/h. Then with continued heating excess cyclohexyl acrylate was distilled off to such an extent that the temperature of the reaction mixture at the base of the column was 135° C. Then the water of reaction was distilled off at 135° C. over 18 h using isooctane as azeotropic entrainer. Thereafter preparative column chromatography of the distillation residue over silica gel using 20/80 ethyl acetate/hexane as mobile phase yielded 46 g (26%) of cyclohexyl 2-hydroxymethylacrylate,
127 g (73%) of dicyclohexyl 2,2'-[oxybis(methylene)]bis-2-propenoate, and
2 g (1%) of higher homologs of the oxadimethacrylic.

b) Workup by Crystallization

A mixture of 308 g (2 mol) of cyclohexyl acrylate, 30 g (1 mol) of paraformaldehyde, 11.2 g (0.1 mol) of DABCO ® and 172 mg of hydroquinone monomethyl ether was heated at 75° C. for 6 h while air was pumped through the mixture at the same time at a rate of 10 l/h. Then excess cyclohexyl acrylate was distilled off under reduced pressure. Then the water of reaction was distilled off with slow heating to 135° C. over 12 h using isooctane as azeotropic entrainer. After the water of reaction had been distilled off, the residue was cooled down to 60° C., admixed with 340 g of n-hexane and stirred at 60° C. for a further hour. Thereafter the bottom layer was separated off and the top layer was cooled down with stirring to 0° C. This precipitated some of the dicyclohexyl ester in the form of fine white crystals. Filtration, washing with 100 ml of 0° C. n-hexane and drying at 25° C./100 mbar yielded 142 g (81%) of the dicyclohexyl ester in a purity of 96%. Concentrating the mother liquor under reduced pressure, renewed addition of n-hexane at 60 ° C. and repeated crystallization yielded a further 9 g of the dicyclohexyl ester in a purity of 92%.

We claim:

1. A process for preparing oxadimethacrylics of the formula I $$CH_2=C(A)CH_2-O-CH_2C(A)=CH_2 \quad \text{I}$$

where A is selected from the group consisting of —COOR$^1$, —COR$^1$, —CONR$^2$R$^3$ and —CN and R, R$^2$ and R$^3$ are each defined as follows:

R$^1$ is hydrogen, alkyl, substituted or unsubstituted cycloalkyl or cycloalkylalkyl, hydroxyalkyl, aminoalkyl, N-alkylaminoalkyl, N,N-dialkylaminoalkyl, substituted or unsubstituted aryl or arylalkyl, R$^2$ and R$^3$ are each hydrogen, alkyl, substituted or unsubstituted cycloalkyl or cycloalkylalkyl, substituted or unsubstituted aryl or arylalkyl, comprising the following steps:

(I) reacting an acrylic of the formula II $$H_2C=C(A)H \quad \text{II}$$

with formaldehyde or a formaldehyde donor in the presence of oxygen, with at least one tertiary amine to form an alcohol of the formula III $$H_2C=C(A)CH_2OH; \quad \text{III}$$

(II) subsequently converting the alcohol III by heating in the presence of oxygen and at least one tertiary amine to yield a crude mixture; and (III) adding to the crude mixture obtained in step (II) at least one liquid hydrocarbon having a boiling point of from 20 to 200° C., the weight ratio of hydrocarbon to oxadimethacrylics I being from 1:1 to 100:1, and thereafter separating the crystallized oxadimethacrylics from the reaction mixture.

2. A process for preparing oxadimethacrylics of the formula I $$CH_2=C(A)CH_2-O-CH_2C(A)=CH_2 \quad \text{I}$$

where A is selected from the group consisting of —COOR$^1$, —COR$^1$, —CONR$^2$R$^3$ and —CN and R, R$^2$ and R$^3$ are each defined as follows:

R$^1$ is hydrogen, alkyl, substituted or unsubstituted cycloalkyl or cycloalkylalkyl, hydroxyalkyl, aminoalkyl, N-alkylaminoalkyl, N,N-dialkylaminoalky, substituted or unsubstituted aryl or arylalkyl, R$^2$ and R$^3$ are each hydrogen, alkyl, substituted or unsbstituted cycloalkyl or cycloalkylalkyl, substituted or unsubstituted aryl or arylalkyl, comprising the following steps:

(I) converting an alcohol of the formula III $$H_2C=C(A)CH_2OH$$

into the oxadimethacrylics I, by heating the alcohol in the present of oxygen and at least one tertiary amine yielding a crude mixture; and (II) adding to the crude mixture obtained in step (I) at least one liquid hydrocarbon having a boiling point of from 20° to 200° C., the weight ratio of hydrocarbon to oxadimethacrylics I being from 1:1 to 100:1, and thereafter separating the crystallized oxadimethacrylics I from the reaction mixture.

3. A process for preparing oxadimethacrylics of the general formula I'

$$CH_2=C(A)CH_2-O-CH_2C(B)=CH_2 \quad \text{I'}$$

where A and B are selected from the group consisting of —COOR$^1$, —COR$^1$, —CONR$^2$R$^3$ and —CN with the proviso that A is not the same as B and R$^1$ and R$^2$ and R$^3$ are each defined as follows:

R$^1$ is hydrogen, alkyl, substituted or unsubstituted cycloalkyl or cycloalkylalkyl, hydroxyalkyl, aminoalkyl, N-alkylaminoalkyl, N,N-dialkylaminoalky, substituted or unsubstituted aryl or arylalkyl, R$^2$ and R$^3$ are each hydrogen, alkyl, substituted or unsubstituted cycloalkyl or cycloalkylalkyl, substituted or unsubstituted aryl or arylalkyl, comprising the following steps:

(I) reacting a mixture of two different acrylics of the general formulae II and IIA $$H_2C=C(A)H \quad \text{II}$$

$$H_2C=C(B)H \quad \text{IIa}$$

with formaldehyde or a formaldehyde donor compound in the presence of oxygen, with at least one tertiary amine to form a reaction mixture containing the alcohols of the formulae III and IIIA $$H_2C=C(A)CH_2OH \quad \text{III}$$

$$H_2C=C(B)CH_2OH; \quad \text{IIIa}$$

converting the reaction mixture containing these alcohols into the oxadimethacrylic I′, $CH_2=C(A)CH_2-O-CH_2C(B)=CH_2$, by heating in the presence of oxygen, with at least one tertiary amine yielding a crude mixture; and (III) adding to the crude mixture obtained in step (II) at least one liquid hydrocarbon having a boiling point of from 20° to 200° C. the weight ratio of hydrocarbon to oxadimethacrylics I being from 1:1 to 100:1, and thereafter separating the crystallized oxadimethacrylics from the reaction mixture.

4. A process for preparing oxadimethacrylics of the formula $$CH_2=C(A)CH_2-O-CH_2C(B)=CH_2 \quad \text{I′}$$

where A and B are selected from the group consisting of $-COOR^1$, $-COR^1$, $-CONR^2R^3$ and CN with the proviso that A is not the same as B and $R^1$, $R^2$ and $R^3$ are each defined as follows:

$R^1$ is hydrogen, alkyl, substituted or unsubstituted cycloalkyl or cycloalkylalkyl, hydroxyalkyl, aminoalkyl, N-alkylaminoalkyl, N,N-dialkylaminoalky, substituted or unsubstituted aryl or arylalkyl, $R^2$ and $R^3$ are each hydrogen, alkyl, substituted or unsubstituted cycloalkyl or cycloalkylalkyl, substituted or unsubstituted aryl or arylalkyl, comprising the following steps:

(I) reacting an acrylic II $H_2C=C(A)H$ with formaldehyde or a formaldehyde donor compound in the presence of oxygen, with at least one tertiary amine and in the presence of at least one polymerization inhibitor to form an alcohol III and subsequently reacting of the isolated alcohol III, or of the reaction mixture containing the non-isolated alcohol III, with a further, different alcohol IIIA $H_2C=C(B)CH_2OH$ by heating in the presence of oxygen, of at least one tertiary amine and of at least one polymerization inhibitor to form the oxadimethacrylic I, $CH_2=C(A)CH_2-O-CH_2C(B)=CH_2$, yielding a crude mixture; and (II) by adding to the crude mixture obtained in step (I) at least one liquid hydrocarbon having a boiling point of from 20° to 200° C., the weight ratio of hydrocarbon to oxadimethacrylics I being from 1:1 to 100:1, and thereafter separating the crystallized oxadimethacrylics I from the reaction mixture.

5. A process for preparing oxadimethacrylics of the formula $$CH_2=C(A)CH_2-O-CH_2C(B)=CH_2 \quad \text{I′}$$

where A and B are selected from the group consisting of $-COOR^1$, $-COR^1$, $-CONR^2R^3$ and $-CN$ with the proviso that A is not the same as B and $R^1$, $R^2$ and $R^3$ are each defined as follows:

$R^1$ is hydrogen, alkyl, substituted or unsubstituted cycloalkyl or cycloalkylalkyl, hydroxyalkyl, aminoalkyl, N-alkylaminoalkyl, N,N-dialkylaminoalkyl, substituted or unsubstituted aryl or arylalkyl, $R^2$ and $R^3$ are each hydrogen, alkyl, substituted or unsubstituted cycloalkyl or cycloalkylalkyl, substituted or unsubstituted aryl or arylalkyl, comprising the following steps:

(I) converting a mixture of two different alcohols $CH_2=C(A)CH_2OH$ III and $H_2C=C(B)CH_2OH$ IIIA into the oxadimethacrylic I′, $CH_2=C(A)CH_2-O-CH_{22}C(B)=CH_2$ by heating in the presence of oxygen, of at least one tertiary amine and of at least one polymerization inhibitor, yielding a crude mixture; and (II) adding to the crude mixture obtained in step (I) at least one liquid hydrocarbon having a boiling point of from 20° to 200° C., the weight ratio of hydrocarbon to oxadimethacrylics I being from 1:1 to 100:1, and thereafter separating the crystallized oxadimethacrylics I from the reaction mixture.

* * * * *

UNITED STATES PATENT AND TRADEMARK OFFICE
CERTIFICATE OF CORRECTION

PATENT NO.: 5,393,917

DATED: February 28, 1995

INVENTOR(S): BESECKE et al.

It is certified that error appears in the above-identified patent and that said Letters Patent is hereby corrected as shown below:

On title page, item [57], line 6 from the bottom, "substituted", second occurrence, should read --unsubstituted--.

On title page, item [57], line 3 from the bottom, insert --which-- before "comprises".

Column 10, claim 2, line 40, "present" should be --presence--.

Column 12, claim 5, line 34, "⊚" should be -- = --.

Signed and Sealed this

Nineteenth Day of September, 1995

Attest:

BRUCE LEHMAN

*Attesting Officer*　　　　*Commissioner of Patents and Trademarks*